United States Patent [19]
Amaral et al.

[11] Patent Number: 5,976,808
[45] Date of Patent: Nov. 2, 1999

[54] ASSAYS FOR IDENTIFYING AGENTS WHICH AFFECT REGULATORS OF UCP3 GENE EXPRESSION

[75] Inventors: M. Catherine Amaral; Ning Zhang; Jin-Long Chen, all of S. San Francisco, Calif.

[73] Assignee: Tularik Inc., South San Francisco, Calif.

[21] Appl. No.: 09/169,203

[22] Filed: Oct. 9, 1998

Related U.S. Application Data

[62] Division of application No. 08/948,277, Oct. 9, 1997, Pat. No. 5,849,581.

[51] Int. Cl.⁶ .............................. C12Q 1/68; C12Q 1/02
[52] U.S. Cl. .................................. 435/6; 435/29

[58] Field of Search ............................................. 435/6, 29

[56] References Cited

PUBLICATIONS

Boss et al, FEBS Letters, vol. 408, No. 1: pp. 39–42, May 12, 1997.

*Primary Examiner*—Terry McKelvey
*Attorney, Agent, or Firm*—Richard Aron Osman

[57] ABSTRACT

The invention relates to regulators of UCP3 gene transcription, including novel UCP3 transcriptional promoters. UCP3 promoters are used in diagnosis and pharmaceutical development. In particular, transfected cells comprising UCP3 transcriptional regulators operably linked to a reporter are used in high-throughput pharmaceutical screens.

16 Claims, 2 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 2000 base pairs
       (B) TYPE: nucleic acid
       (C) STRANDEDNESS: double
       (D) TOPOLOGY: linear    (ii) MOLECULE TYPE: DNA (genomic)

(xi) SEQUENCE DESCRIPTION: SEQ ID NO:1:

```
AAGCTTTGCA CTTGAACATC CATGCTTCTG ACCACCTGCC CTGTGACGCT GGCTCTGTGC      60

CCCAGTCCAG AAAAGACTTC TGCCTACTCC TCCTCTGCCC TACCCAGTTA ACTCCCTTTC     120

CTTCCCTCCC TTCTGCTTCT CACTCCTCCC CTCCCTTCTC TTCTTCTTCT CCCCTTCCCC     180

CATCACCTGG GGCCCGATTC AGCTGTGCCC AGCCCTTACT CTGAGTGCCC ACAGATGGAG     240

CCTCCAGTAG CTTCTGTGGG GCACCCTTCC ACCAGGTCCC AGCTCCCTTG GCTCCAGCAG     300

TGTCCATGCT AAAGCCTCCA AGTGTCATGT TGGAGAGAAT GGTGTTCACA GTAGATAAGC     360

CCAAAATGCC TTACAGTTTA CAGGCTGGAG TCAGGCCCCG CCACGTTGCT GGCTACATGA     420

CTTCCCTGAG ATTCCATTTC CTCCTCAGTA AAATAAGTGG TAAGATTTTA GGATCCCCAG     480

CACTAAAAAG AAACGAAATA CTGATACAGG CTCCAACATG GATGAATTTT GAAAGCATTA     540

CTATACTAAG TGAAAGAAGC CAGTCACAAA CAAGCACATA TTGGATGATT CCATTTCTAG     600

GAAGTGTTCA GAACAGGCAA ATTTATAGAG ACAGAAAGTA GATTGATTAG TGGTTGCCTG     660

AGGCTGGGGA GCGGGGAAG GGAGGTGACT ACCAATGTGT ATGGAGTTTT TCCAGGGTGA     720

GAGGGTGATG AAAATGTTCT AAAATAGATT GTGTTGATGG TTGTGCCACT CAGAATATAC     780

TAAAAACCAT TTGAATTGTG CACTTGAAAC AGATGAATTG TACGGTATGT GAATTCTATA     840

TCAATAAATC TGTAATTTAA AAAAAAAAAA TTAGGTCGGG TGCAGTGGCT CACACCTATA     900

ATCCCAGCAC TTTGCCAGAC TGAGGCAGGA GGATCACTTA AGCCCAGGAG TTCAAGACCA     960

GCCTGGGGAA CACAGCAAGA CCTCGTCTCT ACTAAAAAAT TTTAAATTAC AAAAAAAAAA    1020

AGTAAAAAAA ATAGAATCCT AATAGTACCT ATCTCATAGG ATTGTGGAAA ATAGTAGTAA    1080

TGTATGTAAA ATATTTAGCA CATAGTAGGC ACAAAGAAAT GACATTATTA TTAAGAGACC    1140

TGGGAGAGCT GTGCCCAGCC TATCGTGGGA GGCCTTGACC TTTGGACTCA AAAGTGGCAG    1200

CAGGTCCACC CCCCCATACA CCCTTGTCAC CAAGGAAGCG TCCACAGCTT AAAGGAGCTA    1260

TATTAAAGCA CCCCAAGTCA AGAGGACTGA ACCAGATCTG GAACTCACTC ACCTCCCCTC    1320

TCACCTCACT GCCCTCACCA GCCAGCCTCT TGTCAAGTGA TCAGGCTGTC AACCAACTTC    1380

TCTAGGATAA GGTTTCAGGT CAGCCCGTGT GTATAAGACC AGTGCCAAGC CAGAAGCAGC    1440

AGAGACAACA GTGAATGACA AGGAGGGGCC ATCCAATCCC TGCTGCCACC TCCTGGGATG    1500

GAGCCCTAGG GAGCCCCTGT GCTGCCCCTG CCGTGGCAGG ACTCACAGGT AAGACCGGTT    1560

TCTCCTCCCT CATCCCTTCC CCTCTCCCTC TCCCTTCTCC TTGTTCTCCC TTTCATTGGA    1620

GGCTTTCAGA GAGCAGCCCC GAGCAGTCAG GGCTCACTAG CTGCAGCTTG TCAGACCTGA    1680

TAGAGATTCA GTCCAGCCGC CACCTTATGA AAAGGGAGCT GTGGCCTTGA TGAGGGTACT    1740

GTGGCAGGGC TGGGGCTTGA ACCCAACACC CGTGTCACTC ACTCAAGACT CACACCCCCT    1800
```

```
TTGCCTTGCT GGCTGCCTCT GGTGGGATTT TGCAAATCCC CATAGACAGG AAGTGGCTTT    1860

CTTCTTTGCC TGCCCCAGAA TCTCTGCGAT TCCTCCAGAG CATAAATCCC TCTCTTTCCA    1920

TGAGGACCCT GGGGCCCTCT TCCTGAGTAG GGATGACAGG GGCACTTCTG ACCTGAGGCG    1980

TGGTCCAGGT CATTTGCTGG                                                2000
```

(2) INFORMATION FOR SEQ ID NO:2:

(i) SEQUENCE CHARACTERISTICS:
        (A) LENGTH: 5436 base pairs
        (B) TYPE: nucleic acid
        (C) STRANDEDNESS: double
        (D) TOPOLOGY: linear     (ii) MOLECULE TYPE: DNA (genomic)

(xi) SEQUENCE DESCRIPTION: SEQ ID NO:2:

```
ACTAGTGACC CAAAAGATCT GTCTATAGCT ACAGCCAGAG CACCGAATGG GACAAGTATC      60

CTCTAAACAC CAAAGATCTC AGGATCTTGA GATGAGGCAC ACAGAAGCTT AAAAGTCTCT     120

CAGAGAACCC AAAGGGTATA TCCACAGTAG ACCACTACCA TTGGTTCTAG TGGAATGAAT     180

GAGGCATTTA CTGCAGAGGC AGTCTCCTTC CAACCTGATC TAAACCAGAT CTTCATGACC     240

CAGTCCTACC CATTCACTGG TCTCATAGCA TCCGAGCCCT CGTCTTGACC TGGCCTGCCC     300

GGGGTTGTGT ATTGAAGCTC TAGTTCATGC CCTCAGAAGT GCCTGGTCTG GAGCAGAGGG     360

CAATATGGAC ACTGGCCTCT TGGCCCTCCC CTGGCCTGAG GTGTTACTTT AGAAGGAAGA     420

ACTGTGAACC AAAAACAACA CCCTTCCTGT TAGCCTAGAC CTCCCCAGAA CACAGAGCTG     480

TACCTCCAGG CTCTGCCAAG CATCCTAGCT TGACACTGCT TATTCTTGGC CACCAGGAAG     540

GCTTGCCTAA GGGCCTGCTC GGCTTGCCCA CCTCCCCCTC AGTGCTTAGA GATCTGGACT     600

GACAGGGATA GTCCTGACTA TTTGCCCAGC CCCCTTGGCC ATGGTTAGGA AACTAGCACC     660

CAAGCAGCAG AGAGGACACA AGCTCATTCC CCTTACCCCA TTCTTTGGGT AGGTCACTGT     720

GTCTTGCCTG TTTTACTCTG AGCTGTGAAG CCAGGATCTG CTGTCATTTC TGCCTCCTGT     780

TGACGTGTAT TGTTCTATAA AAAGGAATAA TGGGATTTCT AAGTGTGCTC ATCCTTGACC     840

CTCTCTAGCC AGGCCTGACC TTTCTTGTTA GCAGGCTCAC GGGGTACAAG CTGGAGAGGT     900

GGAACAGTGT ATTAGGGTCC GTCAGCATGG GAACAAAAAA GATCTACCGG CCTGTGGGGA     960

CAGCCTCCGT TTCTTTCTGC ACTGGCTCTT CCTGCCTGGC CTCCATCTCT TTCCTAGGGG    1020

CCTCATTCTC AGCCCACCAG GCAACTTTGC TATGTAGATC TGAGCCCTTC AGCACAGGAA    1080

CCTGACAAGA TACCAAAAAG GGGAAAGTGG CTGAGCACAC GGCTTTGTCT ATGGTAGCTG    1140

CTCAAGTGGG ATTTCCACCT GCCTCAGCTC TGCCACTCAG AGCTGCACGA CCTTGAACTA    1200

ACTAAGTGCA CCTGACCTTG TGATGTCATG GCCAGGGTTC CACAAGACAG GGTGTATGAG    1260

GTATTTGCAA ACCAGGGACC TAGAGAAAAT GTTAGCCCAA GGACCAGACT CGCCTCTGCA    1320

ATGCTGTATC CTCAGGACTA ATCTAGATGA CTTCCTTCTC TCCAGGACAA GAGTGAAGCC    1380

CACCAGGGGG AGCCCTTGCC CAGAGGCCTT GTCGCCCCAG ACCTTACTCC ATCCCTCCCA    1440

ACCTTCCTGA GGAAGAGACT CGCAGGATTG CACGGATATT TTCTTCCCAG TATTCCAAAA    1500

AGACTGAGGA AACCTGAGGG ACGTGGCTAC CAGCCAGCCT CTCAGCTCTG TAAAGCTTGC    1560

AAGAGACAAC AGGCCTATTT CCCTCAGCAT CCTCAGGCCA CTAGCATCAC CCTATTCCAT    1620

GGGTATCTTG AGACCTAATC AGCTAAGACC AGAGGAGTGT CCCAAACCAC CTAGCAGCTG    1680

CCTACCAGGA CCTCAGCTTC CTTCTGTAAT GAGGTGACTG CTGGAAGTGA GACTCAAGCA    1740

CCCAAGTGTC CCACCCATCT TCTGACTGTG GGGCCTAAGG AGGCCTCTCT GAGCAGAGAA    1800
```

```
ACCAGTGTCC TTGACACAGC CTACTGCTGA CCAGAGCCCA CCTTCTGCTT AAATAGGACA    1860

GGCTATTTTT GCCATAAATA TTGGAAGAAA CATGGAATAA GTATGTACAT AGCTGAGAAA    1920

ATTCCAGAGC CCTGTCCAGC TTGTTTGTTT GGGAATGAGG TATTTTATTG ATATAAATTA    1980

TTTTTATGAT GTATTAATCA ATAGAACAGG GGAATTGCCT CCTTTAAAAC TGTATTCGGT    2040

TGTCTGAAAT TTAACCATGT TTTTAACATA ATGTTTGTTT CTACTCAGCT CTGAAATTCA    2100

TTGCTCTTGC CTTTGTTTTT AATAAAAGTC TGGCATTTGT ATTTGTGTAC AAGTGTTTTT    2160

TGGGTTGGTC ACTGGGAAAA GGTGTTGCAG AAAGAAGGAT ACAGCCATCA CTCCACCACC    2220

TGCAACATGA GTCGCCATGA GACTTGCTAG TTCTTCCAAC TGTCAGATTG ACCCATGTTA    2280

GAGGGATGCT AGTGTTCCAC TTCTGGTGGT TTGGGCTTTT GCTTGCTTGC TTGGTTTGTC    2340

TTTTCCTCTG ATGGCCCTTT AAATCTTGCT CAGCACAGTG AGCGTCCAAC TAAGATCTCG    2400

TCCCCGGTGT GACTCACGAG GGCACTTCTG TCAGAACACA GCCACTTGGG CAGCTACCAT    2460

AGACAAAGTC CTCTGAGGAT AATCTGAACG GAATAGATGT CCAGTGCGTC TGGTAGTGAG    2520

GCGGAAAGGA GCTACCTGAG GGCTCTGCTT GTCACCCTGT GTGTCATTTC TCTAAATCCT    2580

CACAACTCTA TGATGCCCCT CCCACAATTA CCCTCAACAC CATGGAAGTC GGATGCATTG    2640

CTTCTGTATC GGTACAAAGT GCATCAGGAC CGAAGACATA CCCCAGAGAT AAGGACTCAG    2700

ACCAAAGCAG GATACAGGCA GTAAACGCCC TGAATTCGGG CGGTCTCAGG CTGCTAAATC    2760

CAGGGAGGGA TTTCTGGAAG AAACCCGTAC TGGGGTAAAG CCCAGAGAAT GGTATAGACC    2820

AGGTCATGGA CAGCTGCAAA GAGAACCAGA GAATGTTCTG GACCATATCA GTGTCCAGCC    2880

TGGCTGAAAC TGTGGCTCTG GCCTCATCTG GAAGGCACAG ACACGTAGAC TCTGGCTTCG    2940

TATGGTCGCT GTGAAGATCA AATGGGACAT TTCTGAAAAT GCTTCGCTGG CATTTGGCAC    3000

ATAATGGAAG CTTGAGAAAT GTCAGCCCTT CCCACTCTTC CTAAGCACCG GGGTGAATTA    3060

GAGGCAAGCT CACTGGCTAC CCAGAACGCA GAGCACTCCA GCCTCCCATA AGGGCCATGA    3120

ACCTTCAGCC AAACCTGCCC CTCAGATCTC TGTTCCTTGG AGGTCACCTT GCAAACCTGC    3180

CCAGTCCTTA GCCAGGGGTT CCCCTTGCCC CAGGCCTTGC CTTCGGCCAG AACAGAGCTT    3240

CCAGTACCTG GAGTTCCACG TCCCTCGGGG TAAGAAACTT CTAGGTTCCA AGCCTAAGGG    3300

GTAAAGCCTA GGGTGAAGAA GATCACTGCC AAATCCTGAT CCTGTAAATA ACCTGAAGGA    3360

GTCAAGTGAG AACAGGGCCA CAGGAGGGCA CGGGCTGCAG ACAAGGTGAA GGTCTGAGAC    3420

ACAGACGACA TGCCCAATTT GTTATTTACC AGTCTCTCCC AGTGATAGCT CTGAGGCAAC    3480

TTGACTTGCC AAGTTGTACA ACACATTTGT CACCACAACC AGAATGAACC CTGACTTCCT    3540

TATGCATGCC CTCCACAGAT GCCTGGAAAG TATTTCTGGT GACCCAGAGA CTGTAGCAGC    3600

CAACCTTAAA ACTCCCAGCA GAGGTTTGAC TCTAGCTAGG CCTGAGCTCT CCTCCCTCTG    3660

GGTTTCTCCA GAACCTGCTG CCTCTAGTTT GACTTCTACT TGTAGCCCCA GCCCCCACAT    3720

GGTTCCCACA GTCCTGCCCA TGTCCAGATT AATAGTTCCA GACTGAGCTC AAAGCAGTGA    3780

GCAGGTCCTG GTCCAAGAAA CAGGATAGAC AGTCTAGATG TCACAGCACC CACCCTGCCA    3840

TGGCGCTGCG CTCAAGTTCC AAAATGTCCT CTACCTTCTC TGTCCTACTT ATCTCCTCTC    3900

CCCTCTCCTT TTAGTTTCCC TTCTATGCCA CCTGGCTCCC AACTTCAGCT GTGCCCACCC    3960

AGTCTTTAAC CTCAGCGCCT GCAGATGGAC CAGCCTACAG TGGTTGCTGC AAGGGATTTT    4020

GCTCACCCTG CCCCATCTCC GGTCCCAGCA TGTCCATGTC ATGAGGAATC AGGATTGCAG    4080

CTGATAGACC CAAAGTGTGG TATAGGTTAC AGGCAAGTCA GGCCTGCAGT GACCTAGCTG    4140

TCTGTCCTTG ACAGTCAGTT TTCTGTGTAA AGTAAGCATT GACACATGAG GGCTCTACAC    4200
```

-continued

```
AGTACGTCAG TGTCTACCGG TACAGTGCAG TGTGTTAACA CCACTGTGAA AGAAACCAGC    4260

CACAAGAGGC TATACATTCT ATATAATCCT ACTCAAACAA AGCATCTAGA ACAAGCAAAT    4320

TAAGAAGCAG AATAAAGACG AGTGGTTGCC TGAAGCTGGG GGAAGGGAAA GGGGGTGACT    4380

TGTTCTGTTT TTGTCTTTGA GCCATGATGA AAGTGTTCTG AACTAGCATG TAGTAGTTGA    4440

TCAACCAGAC TGTACTAAAC ACTATTGTGT GCTCTATGTG GGCAAATCAC ATGCTGTGTA    4500

CAAAACATCT GTTGTCCTTT GTTTTTAAAT TTAGGATCCT GCTTCCTAGA GATGTGGGAA    4560

ATAGAAGCGC TGTGCCTGAA ATATCAAGCA TATCTTGGCA CCAAGATGTC CTCTACCTTC    4620

TCTGCCCCGT CTTCTCCTCT CCCCTCTTGA GAATGTCAGG CCTCTAAGAA GTGACACCTG    4680

TAACCATTGT ATAGGATCCT GGAGAGCCCC TGTCCTAAGA GACCTTGTCC TTTGGGCTCT    4740

CAAAGGTGAC AAATGCTGTC ACACACCTCC TGGCCACCAA GGTAGCTCTC CTCTTGAAAG    4800

CTCAAAGGAG CCACATTAAA GAGCCCCAGG TCACGGAAGC TAAACCAGAT CTGGAACTCA    4860

CTGGTCCCCT CCCCGCAGCC TGCCTCTTGT CAAGTGATCA GACTGTCAAC TAGCTTCTCA    4920

GAATTAGGTT TCAGGTCAGC TGGTGCACAG GGCCAGTGCC GAGCCAGGGA CAGCAGAGAC    4980

AACAGTGAAT GGTGAGGCCC GGCCGTCAGA TCCTGCTGCT ACCTAATGGA GTGGAGCCTT    5040

AGGGTGGCCC TGCACTACCC AACCTTGGCT AGACGCACAG GTAAGACCCC ATACTCTGCT    5100

CTCCTCTCCC TTTTTCCCTT CCATGGATGC TCACAGCCAG GAGCTTGCTG GGATCACTCA    5160

GCACTGCGTG AGAGACCGAG AGTGAGCCGG TCTAGCTCCC ACCTAGTAAA GATGAAGGAA    5220

CTGCAGGCCT GGGGAGGGCC TTGACTTCCA CATCTATGTG ACTCCTCACA ACTCCCGTGT    5280

TTTGCTGACT CCTCTGCTGG GATCTTACAA ATGCCAAATG AAAAGTGTCC CTCTCCTTTG    5340

GCCCAGGATC CCCACGGAGC ACAAAGCCCT CTCCAGCAAG GATCCTGGGG CCCTTCCTGG    5400

GTAAAAATAA TGAGGGCACT CTGGCCTGAA GCCTGG                              5436
```

ASSAYS FOR IDENTIFYING AGENTS WHICH AFFECT REGULATORS OF UCP3 GENE EXPRESSION

This is a divisional application under 35 U.S.C. 120 of U.S. Ser. No. 08/948,277, filed Oct. 9, 1997, now U.S. Pat. No. 5,849,581, which is incorporated herein by reference.

INTRODUCTION

1. Field of the Invention

The field of this invention is the transcriptional promoter of the UCP3 gene and its use in drug screening.

2. Background

A mitochondrial protein called uncoupling protein (UCP1) is thought to play an important role in the body's regulation of energy utilization. Such regulation provides wide spread physiological controls including body weight, appetite, glucose metabolism, temperature, immune responses, etc. Mechanistically, UCP1 is thought to create a pathway that allows dissipation of the proton electrochemical gradient across the inner mitochondrial membrane in brown adipose tissue, without coupling to any other energy consuming process (for review, see Nicholis & Locke (1984) Physiol Rev 64, 1–64). Unfortunately, the role of UCP1 in physiologies such as body weight regulation in large adult mammals such as people, cattle, pigs, etc. is likely to be limited, since there is little brown adipose tissue in such animals.

UCP2 is a second, related uncoupling protein that is much more widely expressed in large adult mammals (see, e.g. Fleury et al. (1997) Nature Genetics 15, 269–272 and Tartaglia et al. (1996) WO96/05861). Consistent with a role in the regulation of energy utilization generally, and in diabetes and obesity in particular, the UCP2 gene is upregulated in response to fat feeding and maps to regions of the human and mouse genomes linked to hyperinsulinaemia and obesity. Accordingly, upregulators of this gene hold great therapeutic promise for these diseases. To provide regulators of UCP2 gene expression, we cloned the endogenous promoter of the human UCP2 gene and identified various deletion mutants having transcriptional regulatory activity (U.S. Ser. No. 08/846,012, filed Apr. 25, 1997).

UCP3 is a third, related uncoupling protein also widely expressed in large adult mammals. Accordingly, upregulators of this gene hold great therapeutic promise for diseases such as hyperinsulinaemia and obesity. To provide regulators of UCP3 gene expression, we have cloned the endogenous promoter of natural UCP3 genes and identified various deletion mutants having transcriptional regulatory activity.

SUMMARY OF THE INVENTION

The invention provides methods and compositions relating to the UCP3 gene transcriptional promoter. The compositions include recombinant regulators of gene expression comprising the UCP3 promoter of at least one of SEQ ID NOS:1 and 2, or a deletion mutant thereof at least 50 bp in length having cis transcriptional regulatory activity. Exemplary such deletion mutants comprise at least one of SEQ ID NO:1, bases 411–460, bases 461–510, bases 401–563, bases 319–326, bases 98–104, bases 49–56, bases 49–104 and bases 547–554. In preferred embodiments, the regulators comprise at least one of a GC/SP1, GH-TRE and PR/GR binding site. In further embodiments, the regulators comprise a 5' untranslated UCP3 gene exon. Frequently, the regulators may further comprise a UCP3 or non-UCP3 core promoter operatively joined to said mutant.

The invention also provides hybridization probes and replication/amplification primers having a hitherto novel UCP3 specific sequence contained in SEQ ID NO:1 or 2 (including its complement and analogs and complements thereof having the corresponding sequence, e.g . in RNA) and sufficient to effect specific hybridization thereto (i.e. specifically hybridize with the corresponding SEQ ID NO:1 or 2 in the presence of genomic DNA). Such primers or probes are at least 12, preferably at least 24, more preferably at least 36 bases in length.

The invention also provides cells and vectors comprising the disclosed UCP3 regulators, including cells comprising such regulators operably linked to non-UCP3 genes. Such cells find used in the disclosed methods for identifying agents which regulate the activity of a UCP3 promoter. In an exemplary such method, the cells are contacted with a candidate agent, under conditions wherein, but for the presence of said agent, the gene exhibits a first expression; detecting the presence of a second expression of the gene, wherein a difference between said first and said second expression indicates said agent regulates the activity of a UCP3 gene promoter.

The invention also provides other assays for transcriptional regulators including transcription complex formation assays. An exemplary such assay involves combining a DNA comprising a disclosed regulator with a transcription factor and a candidate agent, under conditions wherein, but for the presence of said agent, the regulator and transcription factor form a first association; detecting the presence of a second association of the regulator and transcription factor, wherein a difference between the first and second associations indicates the agent modulates the association of a UCP3 promoter and transcription factor. The subject nucleic acid regulators also find a variety of other applications, including uses in diagnosis. In particular, hybridization probes and PCR primers derived from the disclosed promoters are used to identify genetic mutations in samples comprising a UCP3 gene.

DETAILED DESCRIPTION OF THE INVENTION

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1 or 2, or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is sometimes advantageous to use nucleic acids comprising other bases or nucleotide analogs to provide modified stability, etc.

The subject nucleic acids find a wide variety of applications including use as hybridization probes, PCR primers, therapeutic nucleic acids, etc.; use in detecting the presence of UCP3 genes and gene transcripts, in detecting or amplifying nucleic acids encoding additional UCP3 homologs and structural analogs, in gene therapy applications and in a variety of screening assays.

In diagnosis, UCP3-promoter specific hybridization probes find use in identifying wild-type and mutant UCP3 alleles in clinical and laboratory samples. Mutant alleles are used to generate allele-specific oligonucleotide (ASO) probes for high-throughput clinical diagnoses. In therapy, therapeutic UCP3 nucleic acids are used to modulate cellular expression or intracellular concentration or availability of active UCP3. For example, UCP3 nucleic acids are used to modulate cellular expression or intracellular concentration or availability of active UCP3 protein. UCP3 inhibitory nucleic acids are typically antisense: single-stranded sequences comprising complements of the disclosed natural UCP3 transcript sequences, particularly the untranslated exon 1. Antisense modulation of the expression of a given UCP3 protein may employ antisense nucleic acids operably linked to gene regulatory sequences. Cells are transfected with a vector comprising a UCP3 sequence with a promoter sequence oriented such that transcription of the gene yields an antisense transcript capable of binding to endogenous UCP3 encoding mRNA. Alternatively, single-stranded antisense nucleic acids that bind to genomic DNA or mRNA encoding UCP3 protein may be administered to the target cell, in or temporarily isolated from a host, at a concentration that results in a substantial reduction in expression of the targeted protein. An enhancement in UCP3 expression is effected by introducing into the targeted cell type UCP3 nucleic acids which increase the functional expression of the corresponding gene products. Such nucleic acids may be UCP3 expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying pharmacological agents or lead compounds for agents active at the level of UCP3 gene transcription. The methods are amenable to automated, cost-effective high throughput screening of chemical libraries for lead compounds. A wide variety of assays for transcriptional regulators are provided including cell-based transcription assays, promoter-protein binding assays, etc. For example, the disclosed luciferase reporter constructs are used to transfect cells such as HeLa cells for cell-based transcription assays. Specifically, HeLa cells are plated onto microtiter plates and used to screen libraries of candidate agents for lead compounds which modulate the transcriptional regulation of the UCP3 gene promoter, as monitored by luciferase expression. An exemplary promoter-protein binding assay is described below. The following examples, exemplary promoter deletion mutants and screening assays are offered by way of illustration and not by way of limitation.

EXAMPLES

Transfection of cultured HeLa cells:

Transient transfections were carried out using cultured HeLa cells by calcium phosphate precipitation. 5 ug of promoter-luciferase plasmid DNA were co-transfected with either 1 ug of pMSV expression vector or 1 ug of pMSV-TR expression vector. Samples were co-precipitated with 2 ug of salmon sperm DNA and 0.2 ug of a β-galactosidase internal control expression vector, then applied atop adherent HeLa cells in 6 well tissue culture plates. After 16 hr cells were washed in phosphate buffered saline and refed with fresh DMEM/F12 culture medium supplemented with 10% fetal bovine serum. After an additional 24 hr cells were harvested, lysed and assayed for luciferase and β-galactosidase enzymatic activity according to manufacturer's recommendations (Promega).

Isolation of human and mouse UCP3 genomic clones.

Genomic clones containing the promoter region, the first exon and the remaining 5' untranslated region of the human and mouse UCP3 gene were obtained by hybridization screening of bacteriophage 1 libraries using PCR amplified probes derived from hUCP3 and mUCP3 encoding sequences. The clones were further confirmed by rehybridization using PCR probes derived from 5' untranslated region sequence, which were obtained from RACE PCR amplification. Genomic clones were subcloned into pBluescript KSII (Stratagene), and then sequenced using an Applied Biosystems DNA sequencer. The promoter sequences were subjected to BLAST search on the NCBI server; no homologies to any known sequence were found. Indentically conserved oligonucleotides (see alignment, Table 1) are used in primers and probes for UCP3 genes.

The DNA sequence of the first untranslated exon and upstream DNA of the human and mouse UCP3 genes are shown in SEQ ID NOS:1 and 2, respectively. A number of transcription factor binding sites, splice sites and transcriptional start sites for the human and mouse genes are are shown in Tables I and II, respectively.

TABLE I

Human UCP3 gene transcriptional start, splice and factor binding sites.

| SITE | SEQ ID NO: 1, nucleotides |
|---|---|
| c-Myc | 1132–1138 |
| IBP-1 | 1355–1360 |
| C/EBP | 1006–1013 |
| NF-IL6 | 266–274 |
| GH-CSE2 | 843–849 |
| HNF5 | 566–572 |
| AP-1 | 1944–1950 |
| START SITE | 1461, 1399–1548 |
| HiNF-A | 1115–1121 |
| AP-2 | 961–968 |
| HC3 | 269–274 |
| GCF | 396–403 |
| GH-CSE1 | 853–859 |
| GR | 602–1607 |
| AP-2 | 1525–1532 |
| INTRON I | 1549–2000 |

TABLE II

Mouse UCP3 gene transcriptional start, splice and factor binding sites.

| SITE | SEQ ID NO: 2, nucleotides |
|---|---|
| c-Myc | 4716–4722 |
| gamma IRE | 4851–4859 |
| PR | 4861–4869 |
| C/EBP | 4287–4295 |
| SRF | 3915–3925 |
| NF-IL6 | 3204–3214 |
| HiNF-A | 2968–2976 |
| AP-1 | 2410–2418 |
| Insulin-Responsive | 1152–1159 |
| AP-2 | 293–301 |
| ApoE-B2 | 5381–5393 |
| EXON | 4935–5080 |
| MyoD | 4675–4681 |
| NF-kB | 4701–4712 |
| NFIL6 | 4405–4414 |
| MyoD | 3929–3935 |
| AP-2 | 3706–3714 |
| p53 | 3062–3072 |
| b-α-tabuli | 2801–2810 |
| GH-CSE1 | 1974–1982 |

TABLE II-continued

Mouse UCP3 gene transcriptional start, splice and factor binding sites.

| SITE | SEQ ID NO: 2, nucleotides |
|---|---|
| CREB | 791–799 |
| GcF | 4996–5003 |
| START | 4935–4948 |
| INTRON | 5081–5436 |

Deletion mutant construction and activity analysis

The promoter activity of the 5' flanking region of human UCP3 gene and a variety of deletion mutants thereof are conveniently screened in a transient transfection assay using mammalian cell lines. An exemplary assay is the HeLa-cell based luciferase reporter assay of FIGS. 1 and 2. Selected promoter deletions are amplified by PCR using targeting primers. Amplification primer pairs for exemplified deletions are as follows:

| Tagged/untagged endonuclease site | Nucleotide Sequence |
|---|---|
| att-MluI | ATTACGCGT |
| att-Hind III | ATTAAGCTT |
| att-EcoRl | ATTGAATTC |
| MluI (core) | CGCG |

H1: att-MluI- (SEQ ID NO:1, nucleotides 1-20)
    att-Hind III (reverse compliment of SEQ ID NO:1, nucleotides 1981-2000)

H2  att-MluI- (SEQ ID NO:1, nucleotides 1-20)
    att-Hind III - (reverse compliment of SEQ ID NO:1, nucleotides 1529-1548)

H3  att-MluI- (SEQ ID NO:1, nucleotides 200-219)
    att-Hind III- (reverse compliment of SEQ ID NO:1, nucleotides 1529-1548)

H4  att-MluI - (SEQ ID NO:1, nucleotides 1091-1110)
    att-Hind III - (reverse compliment of SEQ ID NO:1, nucleotides 1529-1548)

H5  att-MluI (SEQ ID NO:1, nucleotides 1286-1306)
    att-Hind III - (reverse compliment of SEQ ID NO:1, nucleotides 1529-1548)

H6  att-MluI - (SEQ ID NO:1, nucleotides 1462-1482)
    att-Hind III - (reverse compliment of SEQ ID NO:1, nucleotides 1529-1548)

H7  att-MluI - (SEQ ID NO:1, nucleotides 1-20)
    att-Hind III - (reverse compliment of SEQ ID NO:1, nucleotides 1068-1090)

H8  att-MluI - (SEQ ID NO:1, nucleotides 1286-1306)
    att-Hind III - (reverse compliment of SEQ ID NO:1, nucleotides 1441-1461)

M1  att-MluI - (SEQ ID NO:2, nucleotides 1-25)
    att-Hind III - (reverse compliment of SEQ ID NO:2, nucleotides 5411-5436)

M2  att-MluI - (SEQ ID NO:2, nucleotides 1-25)
    att-Hind III - (reverse compliment of SEQ ID NO:2, nucleotides 5054-5080)

M3  att-MluI - (SEQ ID NO:2, nucleotides 3751-3778)
    att-Hind III - (reverse compliment of SEQ ID NO:2, nucleotides 5054-5080)

M4  att-MluI - (SEQ ID NO:2, nucleotides 3940-3967)
    att-Hind III - (reverse compliment of SEQ ID NO:2, nucleotides 5054-5080)

```
M5    att-MluI - (SEQ ID NO:2, nucleotides 4581-4612)
      att-Hind III - (reverse compliment of SEQ ID NO:2, nucleotides 5054-5080)

M6    att-MluI - (SEQ ID NO:2, nucleotides 4840-4867)
      att-Hind III - (reverse compliment of SEQ ID NO:2, nucleotides 5054-5080)

M7    att-MluI - (SEQ ID NO:2, nucleotides 4930-4958)
      att-Hind III - (reverse compliment of SEQ ID NO:2, nucleotides 5054-5080)
```

The deletions may be recombined in any desired variation. For example internal deletions are readily prepared by amplifying both 5' and 3' deletions followed by ligation. Alternatively, a UCP3 promoter deletion may be fused with non-UCP3 promoter element(s) to form heterohybrid promoters. Internal deletions and heterohybrid constructs are exemplified as follows:

```
M8·1a&1b pair; 2a&b pair
     1a.  att-MluI - (SEQ ID NO:2, nucleotides 1-25)
     1b.  att-EcoR1 - (reverse compliment of SEQ ID NO:2, nucleotides 3727-3751)
     2a.  att-EcoR1 - (SEQ ID NO:2, nucleotides 4840-4870)
     2b.  att-Hind III - (reverse compliment of SEQ ID NO:2, nucleotides 5054-5080)

M9   1a.  att-MluI - (SEQ ID NO:2, nucleotides 3249-3274)
     1b.  att-EcoR1 - (reverse compliment of SEQ ID NO:2, nucleotides 3727-3751)
     2a.  att-EcoR1 - (SEQ ID NO:2, nucleotides 4840-4870)
     2b.  att-Hind III - (reverse compliment of SEQ ID NO:2, nucleotides 5054-5080)

M10  att-MluI- (SEQ ID NO:2, nucleotides 1-25)
     att-EcoR1- (reverse compliment of SEQ ID NO:2, nucleotides 3727-3751)

M11  att-MluI - (SEQ ID NO:2, nucleotides 3940-3967)
     att-EcoR1- (reverse compliment of SEQ ID NO:2, nucleotides 4910-4935)

M12  1a.  att-MluI- (SEQ ID NO:2, nucleotides 3940-3967)
     1b.  att-EcoR1 - (reverse compliment of SEQ ID NO:2, nucleotides 4823-4842)
     2a.  att-EcoR1 - (SEQ ID NO:2, nucleotides 4863-4887)
     2b.  att-EcoR1 - (reverse compliment of SEQ ID NO:2, nucleotides 4910-4935)

M13 &M14 - Oligo anealing no PCR
MluI - (SEQ ID NO:2, nucleotides 4843-4862)
MluI - (reverse compliment of SEQ ID NO:2, nucleotides 4843-4862)
```

Figure 1:
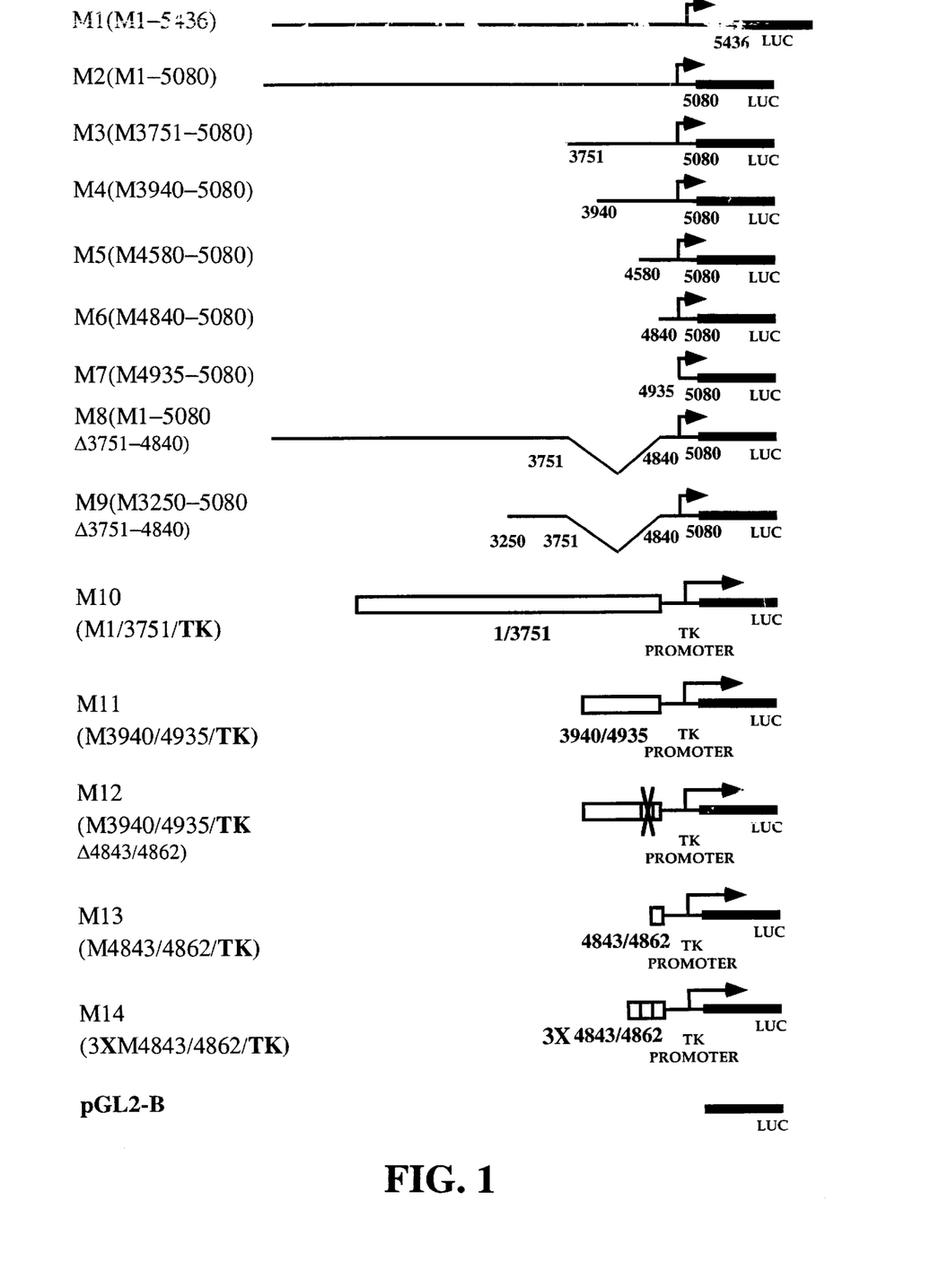
FIG. 1. Diagram of mUCP3 promoter constructs driving expression of luciferase enzymatic activity in CaPO$_4$ transfected HeLa cells. Cells are harvested 18 hrs post transfection and assayed for luciferase.
Figure 2:
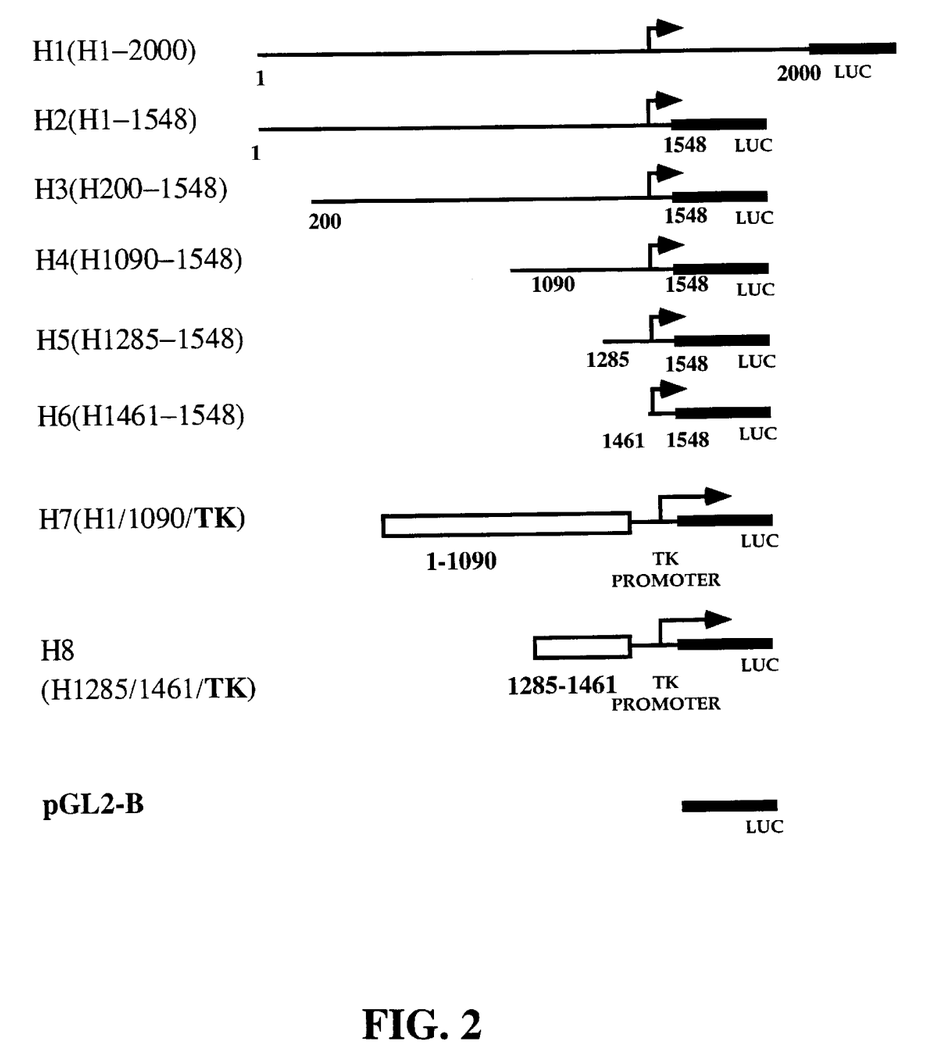
FIG. 2. Diagram of hUCP3 promoter constructs driving expression of luciferase enzymatic activity in CaPO$_4$ transfected HeLa cells. Cells are harvested 18 hrs post transfection and assayed for luciferase.

The PCR fragments are restriction enzyme digested by MluI and HindIII, and then subcloned into MluI and HindIII sites of pGL-2B or pGL-2P (Promega). Transient transfections are carried out using cultured HeLa cells by calcium phosphate precitation method. After 40 hours, cells are harvested, lysed and assayed for luciferase activity. Exemplary mutants are shown to a range of transcriptional activity (FIGS. 1, 2).

Protocol for AP-2 - UCP3 gene promoter binding assay.

A. Reagents:

Neutralite Avidin: 20 µg/ml in PBS.

Blocking buffer: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P AP-2 10× stock: $10^{-6}$–$10^{-8}$ M "cold" AP-2 supplemented with 200,000–250,000 cpm of labeled AP-2 (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM NaVo$_3$ (Sigma # S-6508) in 10 ml of PBS.

Oligonucleotide stock: (specific biotinylated). Biotinylated oligo at 17 pmole/µl, UCP3 gene promoter containing AP-2 site: (BIOTIN)- (SEQ ID NO:1, bases 950–970).

B. Preparation of assay plates:

Coat with 120 µl of stock N-Avidin per well overnight at 4° C.

Wash 2× with 200 µl PBS.

Block with 150 µl of blocking buffer.

Wash 2× with 200 µl PBS.

C. Assay:

Add 40 µl assay buffer/well.

Add 10 µl compound or extract.

Add 10 µl $^{33}$P-AP-2 (20,000–25,000 cpm/0.1–10 pmoles/well=$10^{-9}$–$10^{-7}$ M final concentration).

Shake at 25C for 15 min.

Incubate additional 45 min. at 25C.

Add 40 µl oligo mixture (1.0 pmoles/40 ul in assay buffer with 1 ng of ss-DNA)

Incubate 1 hr at RT.

Stop the reaction by washing 4× with 200 µl PBS.

Add 150 µl scintillation cocktail.

Count in Topcount.

D. Controls for all assays (located on each plate):

a. Non-specific binding (no oligo added)

b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying agents which modulate the association of a UCP3 transcriptional regulator and a transcription factor, said method comprising steps:

combining said UCP3 transcriptional regulator, said transcription factor and a candidate agent, under conditions wherein, but for the presence of said agent, said regulator and said transcription factor form a first association, said regulator comprising a recombinant nucleic acid comprising SEQ ID NO:1 or 2, or a fragment thereof at least 50 bp in length comprising at least one nucleotide sequence selected from the group consisting of: SEQ ID NO:1, nucleotides 411–460; SEQ ID NO:1, nucleotides 461–510; SEQ ID NO:1, nucleotides 401–563; SEQ ID NO:1, nucleotides 319–326; SEQ ID NO:1, nucleotides 98–104; SEQ ID NO:1, nucleotides 49–56; SEQ ID NO:1, nucleotides 49–104; SEQ ID NO:1, nucleotides 547–554; SEQ ID NO:1, nucleotides 1–1548; SEQ ID NO:1, nucleotides 200–1548; SEQ ID NO:1, nucleotides 1090–1548; SEQ ID NO:1, nucleotides 1285–1548; SEQ ID NO:1, nucleotides 1–1090; SEQ ID NO:1, nucleotides 1285–1461; SEQ ID NO:2, nucleotides 1–5080; SEQ ID NO:2, nucleotides 3751–5080; SEQ ID NO:2, nucleotides 3940–5080; SEQ ID NO:2, nucleotides 4580–5080; SEQ ID NO:2, nucleotides 4840–5080; SEQ ID NO:2, nucleotides 1–3571; SEQ ID NO:2, nucleotides 3940–4935; and SEQ ID NO:2, nucleotides 4843–4862 and having cis transcriptional regulatory activity; and detecting the presence of a second association of said regulator and said transcription factor, wherein a difference between said first and said second association indicates that said candidate agent is an agent which modulates the association of said UCP3 transcriptional regulator and said transcription factor.

2. The method of claim 1, wherein the nucleic acid comprises at least one nucleotide sequence selected from the group consisting of: SEQ ID NO:1, nucleotides 411–460; SEQ ID NO:1, nucleotides 461–510; SEQ ID NO:1, nucleotides 401–563; SEQ ID NO:1, nucleotides 49–104; SEQ ID NO:1, nucleotides 1–1548; SEQ ID NO:1, nucleotides 200–1548; SEQ ID NO:1, nucleotides 1090–1548; SEQ ID: NO:1, nucleotides 1285–1548; SEQ ID NO:1, nucleotides 1–1090; SEQ ID NO:1, nucleotides 1285–1461; SEQ ID NO:2, nucleotides 1–5080; SEQ ID NO:2, nucleotides 3751–5080; SEQ ID NO:2, nucleotides 3940–5080; SEQ ID NO:2, nucleotides 4580–5080; SEQ ID NO:2, nucleotides 4840–5080; SEQ ID NO:2, nucleotides 1–3571; and SEQ ID NO:2, nucleotides 3940–4935.

3. The method of claim 1, wherein the nucleic acid comprises SEQ ID NO:1 or 2, or a fragment thereof at least 50 bp in length comprising at least one nucleotide sequence selected from the group consisting of: SEQ ID NO:1, nucleotides 401–563; SEQ ID NO:1, nucleotides 1–1548; SEQ ID NO:1, nucleotides 200–1548; SEQ ID NO:1, nucleotides 1–1090; SEQ ID NO:2, nucleotides 1–5080; SEQ ID NO:2, nucleotides 3751–5080; SEQ ID NO:2, nucleotides 3940–5080; SEQ ID NO:2, nucleotides 4580–5080; SEQ ID NO:2, nucleotides 4840–5080; SEQ ID NO:2, nucleotides 1–3571; and SEQ ID NO:2, nucleotides 3940–4935.

4. The method of claim 1, wherein the nucleic acid comprises SEQ ID NO:1 or 2.

5. The method of claim 1, wherein the nucleic acid comprises at least one binding site from Table I or II.

6. The method of claim 1, wherein the nucleic acid is operatively joined to a non-UCP3 core promoter.

7. The method of claim 1, wherein the nucleic acid comprises a 5' untranslated UCP3 gene exon.

8. A method for identifying agents which regulate the activity of a UCP3 transcriptional regulator, said method comprising steps:

contacting a cell with a candidate agent, said cell comprising said UCP3 transcriptional regulator comprising a recombinant nucleic acid comprising SEQ ID NO:1 or 2, or a fragment thereof at least 50 bp in length comprising at least one nucleotide sequence selected from the group consisting of: SEQ ID NO:1, nucleotides 411–460; SEQ ID NO:1, nucleotides 461–510; SEQ ID NO:1, nucleotides 401–563; SEQ ID NO:1, nucleotides 319–326; SEQ ID NO:1, nucleotides 98–104; SEQ ID NO:1, nucleotides 49–56; SEQ ID NO:1, nucleotides 49–104; SEQ ID NO:1, nucleotides 547–554; SEQ ID NO:1, nucleotides 1–1548; SEQ ID NO:1, nucleotides 200–1548; SEQ ID NO:1, nucleotides 1090–1548; SEQ ID NO:1, nucleotides 1285–1548; SEQ ID NO:1, nucleotides 1–1090; SEQ ID NO:1, nucleotides 1285–1461; SEQ ID NO:2, nucleotides 1–5080; SEQ ID NO:2, nucleotides 3751–5080; SEQ ID NO:2, nucleotides 3940–5080; SEQ ID NO:2, nucleotides 4580–5080; SEQ ID NO:2, nucleotides 4840–5080; SEQ ID NO:2, nucleotides 1–3571; SEQ ID NO:2, nucleotides 3940–4935; and SEQ ID NO:2, nucleotides 4843–4862 and having cis transcriptional regulatory activity, said regulator operably linked to a non-UCP3 gene, under conditions wherein, but for the presence of said agent, said gene exhibits a first expression;

detecting the presence of a second expression of said gene;

wherein a difference between said first and said second expression indicates that said candidate agent is an agent which regulates the activity of said UCP3 gene transcriptional regulator.

9. A method according to claim 8, wherein said gene is a reporter and said detecting step comprises detecting a colorimetric or luminescent signal of said reporter.

10. A method according to claim 8, wherein said gene is detected by hybridization to a nucleic acid specific for said gene.

11. The method of claim 8, wherein the nucleic acid comprises at least one nucleotide sequence selected from the group consisting of: SEQ ID NO:1, nucleotides 411–460; SEQ ID NO:1, nucleotides 461–510; SEQ ID NO:1, nucleotides 401–563; SEQ ID NO:1, nucleotides 49–104; SEQ ID NO:1, nucleotides 1–1548; SEQ ID NO:1, nucleotides 200–1548; SEQ ID NO:1, nucleotides 1090–1548; SEQ ID NO:1, nucleotides 1285–1548; SEQ ID NO:1, nucleotides 1–1090; SEQ ID NO:1, nucleotides 1285–1461; SEQ ID NO:2, nucleotides 1–5080; SEQ ID NO:2, nucleotides 3751–5080; SEQ ID NO:2, nucleotides 3940–5080; SEQ ID NO:2, nucleotides 4580–5080; SEQ ID NO:2, nucleotides 4840–5080; SEQ ID NO:2, nucleotides 1–3571; and SEQ ID NO:2, nucleotides 3940–4935.

12. The method of claim 8, wherein the nucleic acid comprises SEQ ID NO:1 or 2, or a fragment thereof at least 50 bp in length comprising at least one nucleotide sequence selected from the group consisting of: SEQ ID NO:1, nucleotides 401–563; SEQ ID NO:1, nucleotides 1–1548; SEQ ID NO:1, nucleotides 200–1548; SEQ ID NO:1, nucleotides 1–1090; SEQ ID NO:2, nucleotides 1–5080; SEQ ID NO:2, nucleotides 3751–5080; SEQ ID NO:2, nucleotides 3940–5080; SEQ ID NO:2, nucleotides 458–5080; SEQ ID NO:2, nucleotides 4840–5080; SEQ ID NO:2, nucleotides 1–3571; and SEQ ID NO:2, nucleotides 3940–4935.

13. The method of claim 8, wherein the nucleic acid comprises SEQ ID NO:1 or 2.

14. The method of claim 8, wherein the nucleic acid comprises at least one binding site from Table I or II.

15. The method of claim 8, wherein the nucleic acid is operatively joined to a non-UCP3 core promoter.

16. The method of claim 8, wherein the nucleic acid comprises a 5' untranslated UCP3 gene exon.

* * * * *